United States Patent [19]

Norell et al.

[11] Patent Number: 4,961,918
[45] Date of Patent: Oct. 9, 1990

[54] PROCESS FOR PRODUCTION OF CHLORINE DIOXIDE

[75] Inventors: Maria Norell, Linjevägen; Anders Dahl, Ängsövägen; Ursula Söderberg, Fyrväpplingsvägen, all of Sweden

[73] Assignee: Eka Nobel AB, Surte, Sweden

[21] Appl. No.: 310,619

[22] Filed: Feb. 15, 1989

[30] Foreign Application Priority Data

Oct. 11, 1988 [SE] Sweden ............................ 8803606-6

[51] Int. Cl.$^5$ ..................... C01B 11/02; C07C 29/74
[52] U.S. Cl. ................................. 423/479; 423/478; 568/913
[58] Field of Search ............... 423/479, 478; 568/917, 568/918, 913

[56] References Cited

U.S. PATENT DOCUMENTS

| 3,563,702 | 2/1971 | de Vere Partridge et al. | 423/478 |
|---|---|---|---|
| 3,764,627 | 10/1973 | Prinz | 568/918 |
| 3,864,456 | 2/1975 | Winfield et al. | 423/478 |
| 3,933,988 | 1/1976 | Rosen | 423/480 |
| 4,081,520 | 3/1978 | Swindells et al. | 423/478 |
| 4,145,401 | 3/1979 | Swindells et al. | 423/478 |
| 4,465,658 | 8/1984 | Fredette | 423/478 |
| 4,473,540 | 9/1984 | Fredette | 423/479 |
| 4,696,720 | 9/1987 | Kiser | 568/917 |
| 4,770,868 | 9/1988 | Norell | 423/479 |

FOREIGN PATENT DOCUMENTS

| 1088957 | 11/1980 | Canada . | |
| 1149131 | 7/1983 | Canada | 423/478 |
| 1300537 | 8/1969 | Fed. Rep. of Germany | 568/917 |
| 2242354 | 8/1973 | France | 568/917 |
| 171058 | 6/1949 | Sweden . | |

OTHER PUBLICATIONS

"The Composition of Condensates from the Evaporation of Sulfite Spent Liquor", Rexfelt et al., Svensk Papperstidning arg. 73, No. 21, Nov. 15, 1970, pp. 689–695.

Primary Examiner—John Doll
Assistant Examiner—Brian M. Bolam
Attorney, Agent, or Firm—Burns, Doane, Swecker & Mathis

[57] ABSTRACT

The present invention relates to a process for production of chlorine dioxide by reacting in a reaction vessel an alkali metal chlorate, sulfuric acid and methanol as a reducing agent. A reaction medium is maintained at a temperature from about 50° C. to about 100° C. and is subjected to a subatmospheric pressure sufficient to effect evaporation of water whereby a mixture of chlorine dioxide and water vapor is withdrawn from an evaporation region in the reaction vessel and alkali metal sulfate is precipitated in a crystallization region in the reaction vessel. Raw methanol purified by separation and adsorption is used as reducing agent. The raw methanol is purified by dilution with water whereby an unpolar phase is separated and and the remaining methanol-water phase is contacted by an adsorbing agent. The adsorbing agents used can be zeolites, active carbon or polymer adsorbing agents.

10 Claims, No Drawings

PROCESS FOR PRODUCTION OF CHLORINE DIOXIDE

The present invention relates to a process for production of chlorine dioxide from an alkali metal chlorate, a mineral acid and a reducing agent. The process is S carried out in a vessel operated under subatmospheric pressure, whereby water is evaporated and withdrawn together with chlorine dioxide and the alkali metal salt of the mineral acid is crystallized within the reaction vessel and withdrawn therefrom. According to the invention the reducing agent utilized is a methanolic condensate, which is purified by separation and adsorption.

Chlorine dioxide used as an aqueous solution is of considerable commercial interest, mainly in pulp bleaching but also in water purification, fat bleaching, removal of phenols from industrial wastes, etc. It is therefore desirable to provide processes by which chlorine dioxide can be efficiently produced.

The predominant chemical reaction involved in such processes is summarized by the formula $$ClO_3^- + Cl^- + 2H^+ \rightarrow ClO_2 + \tfrac{1}{2}Cl_2 + H_2O \qquad [1]$$

The chlorate ions are provided by alkali metal chlorate, preferably sodium chlorate, the chloride ions by alkali metal chloride, preferably sodium chloride, or by hydrogen chloride, and the hydrogen ions by mineral acids, normally sulfuric acid and/or hydrochloric acid. Processes for producing chlorine dioxide are described in e.g. U.S. Pat. Nos. 3,563,702 and 3,864,456.

In existing processes for production of $ClO_2$ there is often also a by-product $Cl_2$ formation, due to the use of chloride ions as reducing agent according to formula [1]. This chlorine by-product has formerly been used as such in the paper mills as a bleaching agent in aqueous solution. Today there is a tendency towards a more extensive chlorine dioxide bleaching for environmental reasons and thus there is a decreasing need for chlorine as a bleaching agent.

It is also known to use other reducing agents, which do not produce chlorine as a by-product. In U.S. Pat. No. 3,933,988 sulfur dioxide is used as a reducing agent and in U.S. Pat. Nos. 4,081,520, 4,145,401, 4,465,658 and 4,473,540 methanol is used as reducing agent. The methanol utility is very low in a process according to e.g. U.S. Pat. No. 4,465,658. The consumption of methanol is 190–200 kg/ton of produced chlorine dioxide whereas the theoretical consumption is only 79 kg/ton according to the formula $$6NaClO_3 + CH_3OH + 4H_2SO_4 \rightarrow 6ClO_2 + CO_2 + 5H_2O + 2Na_3H(SO_4)_2 \qquad [2]$$

Thus only about 40% of the methanol charged is used efficiently in existing processes.

However, the direct reaction between chlorate ions and methanol is very slow and the true reducing agent in this case is chloride ions reacting according to [1]. The chlorine produced is then reacting with methanol to regenerate chloride ions according to the formula $$CH_3OH + 3Cl_2 + H_2O \rightarrow 6Cl^- + CO_2 + 6H^+ \qquad [3]$$

It is therefore often necessary to continously add a small amount of chloride ions in order to obtain a steady production.

A more efficient process with methanol as a reducing agent is described in U.S. Pat. No. 4,770,868. According to this patent it appears that the methanol losses are strongly dependent on the mode of addition of the methanol to the reactor. According to this U.S. patent an improved yield is obtained by introducing the reducing agent in the crystallization zone of the reactor.

The present invention as it appears from the claims provides a process for production of chlorine dioxide with methanol as a reducing agent, where the efficiency of the process is further improved by the use of a methanol rich condensate as the methanol source.

In the preparation of sulfate cellulose the chips are boiled in a pulping solution, called the white liquor. After boiling the spent pulping solution, the black liquor, is separated from the the pulp. The black liquor is evaporated and the residue is passed to the recovery furnace in order to recover valuable chemicals. In the evaporation of black liquor a methanol rich condensate is obtained. A representative composition of such a methanol rich condensate is:
  40–90% methanol
  5–20% ethanol
  0.2–5% mercaptans and other organic compounds, such as terpenes and higher mercaptans. The methanol rich condensate has a very unpleasant odour and constitutes a waste product in the pulp industry, where it usually has been burnt in order not to burden the effluent water. Various methods have been developed to purify the condensate in order to recover the methanol, which is an important raw material in the chemical industry. Thus e.g. CA patent No. 1,088,957 shows a purification process in different steps with i.a. chemical purification.

Now it has surprisingly appeared that by a very simple purification process the methanol rich condensate, hereafter called raw methanol, can be purified so as to enable its use as a reducing agent in the chlorine dioxide process. It is well known that chlorine dioxide generators usually are sensitive to impurities of organic material, which might cause explosive decomposition reactions. It was therefore surprising that the raw methanol by a simple purification step could be converted to a quality giving good operation conditions in a chlorine dioxide reactor, especially in the light of known technology, such as e.g. CA No. 1,088,957, which comprises a number of complicated steps, including energy consuming distillation, and expensive chemicals in order to obtain an acceptable technical raw material. Thus with the ability to utilize raw methanol from the pulp industry in a simple way as a methanol source instead of the considerably more expensive technical grade methanol, the costs for chlorine dioxide production are decreased.

Also methanol rich condensates from other pulp boiling processes can be purified according to the invention, e.g. raw methanol obtained from sulfite pulp boiling and raw methanol from organosolve processes. Today, how ever, the sulfate gulp process is dominating while at the same time the raw methanol from this process is the most contaminated.

The purification process comprises two steps, one separation step and one adsorption step. The raw methanol is diluted with water, whereby a layer of unpolar (i.e., non-polar) organic compounds is easily separated. The water addition appropriately amounts to 0.07 to 4.0 times the amount of raw methanol by volume, preferably 0.2 to 2.0 times. The addition can be made batchwise by admixing in a stirred tank or continuously by mixing the two liquid flows in a pipe, which can be equipped with a static mixer or leading to a separate mixing tank. After admixing the dispersion of raw methanol/water is passed to a vessel for phase separation. This can be designed as a settler, a column or another apropriate device and possibly equipped with special arrangements for droplet separation, e.g. a coalescense filter, packed net structures or the like. The unpolar layer is separated and the remaining methanol-water phase is contacted with an adsorbing agent. The amount of adsorbing agent in relation to methanol-water phase varies depending on the degree of contamination of the raw methanol and on the capacity of the adsorbing agent. The amount is most simply established by laboratory tests. Usually the adsorbing agent has a capacity of keeping an amount of solvent corresponding to 50 to 5000 times its own weight before it needs regeneration.

As useful adsorbing agents there can be mentioned zeolites of different kinds, active carbon and polymer adsorbing agents, such as polyacrylamides, polystyrene divinylbenzene and other macroporous polymer particles.

The contact with the adsorbing agent can be made in different ways. The adsorption can be effected in a fixed or fluidised bed of e.g. zeolite particles. Another possibility is the use of a column packed with the adsorbing agent, or a suspension of raw methanol and the adsorbing agent in a stirred tank. The adsorbing agent can be regenerated in a known manner by means of elution, desorption and/or thermal treating, or be burnt for generation of energy and destruction.

The methanol purified in this manner can be used without disadvantages and in a good yield in an SVP ® (single vessel process) methanol reactor.

In preparation of chlorine dioxide from sodium chlorate in an SVP reactor with methanol purified according to the invention, the reaction is appropriately operated at a temperature of 50°-100° C., preferably 50°-70° C., and a pressure below atmospheric pressure, appropriately at 60-400 mm Hg. At these conditions the reaction medium will boil or water will be evaporated in an amount sufficient to dilute the chlorine dioxide formed to a safe concentration. The acidity in the reactor can be maintained between 2 and 11 N by the addition of sulfuric acid or another mineral acid. In the reactor the sodium salt of the mineral acid is continuously crystallized and separated in an appropriate way. In order to avoid production losses during start and at production changes it is suitable to add small amounts of chloride ions, preferably in the form of sodium chloride, so that the concentration of these in the reactor is within the interval from 0.001 and up to 0.8 moles per liter.

The invention is illustrated by means of the following examples, where parts and percentages mean parts by weight and percentages by weight, unless otherwise is specified.

EXAMPLE 1

Use of raw methanol as a reducing agent.

An SVP chlorine dioxide reactor was operated with a production velocity of 90 g $ClO_2$/h at a temperature of 72° C. and a pressure of 150 mm Hg. A solution with 550 g/l $NaClO_3$ and 7 g NaCl was continuously added with 358 g/h. Methanol was added in the form of a 50% solution in a flow of 30 g/h and 50% sulfuric acid was added in a velocity sufficient to maintain an acidity of 6.0 N. After an operation time of about 1.5 h the reactor had to be closed down due to serious operation disturbances, such as foaming, over-boiling and explosions with flashlike lightenings in the reactor. Simultaneously so called white outs appeared intermittently.

The methanol used was analyzed and was found to contain a dry substance amount of 0.85% and a sulfur amount of 1.9%. Moreover, at dilution with water a formation of different phases was observed, which was interpreted as the existence of more unpolar organic compounds, probably terpenes.

EXAMPLE 2

Use of raw methanol (from the sulfate process) as a reducing agent, which raw methanol is purified according to the process in CA No. 1,088,957.

Raw methanol was purified according to example 2 and 4 in CA No. 1,088,957 with the exception that alkalinization and distillation was not performed.

According to example 2 in CA No. 1,088,957 the following procedure was followed: To 0.5 l raw methanol 120g 30% $H_2SO_4$ was added and the solution was agitated. About 45% precipitated sulfate was filtered away. The heavier unpolar phase was separated by drainage in a separation funnel. The polar phase contained about 63% by weight of methanol.

According to example 4 in CA No. 1,088,957 the following procedure was followed: To 0.5 l raw methanol 120 g residual acid containing 30 g $Na_2SO_4$ and 38 g $H_2SO_4$ were added and the solution was agitated. About 70 g of a precipitation was filtered away. The heavier unpolar phase was separated by drainage in a separation funnel. The polar phase contained about 70% by weight of methanol.

The raw methanol purified in this manner was then used in chlorine dioxide preparation in an SVP methanol reactor. The same process conditions as in example 1 were used. When methanol purified according to example 2 and 4 in CA No. 1,088,957 was used operation disturbances appear in both cases in the form of explosions and flashlike lightenings together with a strongly reduced yield.

EXAMPLE 3

Use of raw methanol (from the sulfate process) according to the present invention.

To 0.5 l raw methanol 120 distilled water was added. The solution was agitated in a separation funnel and the heavier unpolar phase was drained off. Therafter 10 g zeolite (zeolite A) was added to the polar phase and agitated. After a contact time of about 10 minutes the zeolitic mass was separated and the methanolic solution obtained contained 70% by weight of methanol. The purified raw methanol was used for chlorine dioxide production in an SVP methanol reactor under the same experiment conditions as in example 1. The reaction proceeded without operation disturbances such as explosions or foaming and the yield was satisfactory, more than 95%.

An analysis of the raw methanol purified according to the present process of preparation gave the following results:

| Impurity | Percentage of original amount in raw methanol |
|---|---|
| terpenes | 35% |

-continued

| Impurity | Percentage of original amount in raw methanol |
|---|---|
| thioketals | 65% |
| amines | unchanged value |
| ketones | unchanged value |
| dimethylsulfide | unchanged value |

From these values it appears that only the amount of terpenes is strongly reduced. The amount of other impurities decreased somewhat or remained unchanged. It was therefore very surprising that raw methanol purified according to the present process was working in the sensitive chlorine dioxide process.

I claim:

1. A process for production of chlorine dioxide, comprising the steps of:
   reacting in a reaction vessel an alkali metal chlorate, sulfuric acid and purified raw methanol as a reducing agent in proportions to generate chlorine dioxide in a reaction medium maintained at a temperature from about 50° C. to about 100° C. and subjected to a subatmospheric pressure sufficient to effect evaporation of water;
   withdrawing a mixture of chlorine dioxide and water vapor from an evaporation region in the reaction vessel; and
   precipitating alkali metal sulfate in a crystallization region in the reaction vessel;
   wherein the purified raw methanol is obtained by purifying raw methanol from the waste product of a pulp process, the purifying process consisting of diluting the raw methanol with water to form a non-polar phase and a methanol-water phase, separating the phases, and contacting the methanol-water phase with an adsorbing agent, thereby forming purified raw methanol.

2. A process according to claim 1, wherein the adsorbing agent is zeolite.

3. A process according to claim 1, wherein the adsorbing agent is active carbon.

4. A process according to claim 1, wherein the adsorbing agent is a polymer adsorbing agent.

5. A process according to claim 1, wherein the raw methanol comprises a condensate obtained from the black liquor of a sulfate cellulose process.

6. A process according to claim 1, wherein the raw methanol comprises a condensate obtained from the black liquor of sulfate pulp boiling.

7. A process according to claim 1, wherein the raw methanol comprises a condensate obtained from an organosolve process.

8. A method of using a methanolic condensate recovered from a pulp process, comprising the steps of:
   (a) recovering the condensate from a waste stream of the pulp process;
   (b) purifying the condensate by a process consisting of:
      (1) combining the condensate with water to form a multiphase mixture including a non-polar phase and a methanol-water phase;
      (2) separating the non-polar phase from the methanol-water phase;
      (3) contacting the separated methanol-water phase with an adsorbing agent, thereby forming purified raw methanol; and
      (4) separating the purified raw methanol from the adsorbing agent; and
   (c) using the purified raw methanol in a process for the production of chlorine dioxide, the chlorine dioxide process including the step of reducing an alkali metal chlorate with the purified raw methanol in the presence of sulfuric acid.

9. A method according to claim 8, wherein the process for production of chlorine dioxide includes the steps of reacting in a reaction vessel an alkali metal chlorate, sulfuric acid and the purified raw methanol in a reaction medium maintained at a temperature from about 50° C. to about 100° C. and subjected to subatmospheric pressure sufficient to effect evaporation of water, withdrawing a mixture of chlorine dioxide and water vapor from an evaporation region in the reaction vessel, and precipitating alkali metal sulfate in a crystallization region in the reaction vessel.

10. A method according to claim 8 wherein the amount of water combined with the methanol-rich condensate is from about 0.07 to about 4.0 times the amount of raw methanol by volume.

* * * * *